United States Patent [19]

Raif et al.

[11] Patent Number: 4,597,380

[45] Date of Patent: Jul. 1, 1986

[54] ENDOSCOPIC ATTACHMENT TO A SURGICAL LASER

[75] Inventors: Joshua Raif, Kiryat Ono; Eliezer Zair, Bnei Brak, both of Israel

[73] Assignee: Laser Industries Ltd., Tel Aviv, Israel

[21] Appl. No.: 613,338

[22] Filed: May 23, 1984

Related U.S. Application Data

[63] Continuation-in-part of Ser. No. 431,204, Sep. 30, 1982, abandoned.

[51] Int. Cl.⁴ ............................................... A61B 1/06
[52] U.S. Cl. ...................... 128/6; 128/303.1; 128/395; 219/121 LS; 219/121 LU
[58] Field of Search ............... 128/4, 5, 6, 7, 8, 303.1, 128/395; 219/121 L, 121 LS, 121 LT, 121 LU

[56] References Cited

U.S. PATENT DOCUMENTS

| | | | |
|---|---|---|---|
| 3,796,220 | 3/1974 | Brandemeier | 128/303.1 |
| 3,858,577 | 1/1975 | Bass et al. | 128/8 |
| 3,865,113 | 2/1975 | Sharon et al. | 128/303.1 |
| 3,865,114 | 2/1975 | Sharon | 128/303.1 |
| 3,913,582 | 10/1975 | Sharon | 128/303.1 |
| 4,103,680 | 8/1978 | Yoon | 128/6 |
| 4,141,362 | 2/1979 | Wurster | 128/303.1 |
| 4,146,019 | 3/1979 | Bass et al. | 128/6 |
| 4,170,997 | 10/1979 | Pinnow et al. | 128/4 X |
| 4,211,229 | 7/1980 | Wurster | 128/303.1 |
| 4,228,341 | 10/1980 | Zandberg | 219/121 L |
| 4,261,346 | 4/1981 | Wetterman | 128/6 |
| 4,273,110 | 6/1981 | Groux | 128/6 |
| 4,392,485 | 7/1983 | Hiltebrandt | 128/6 |

Primary Examiner—William H. Grieb
Attorney, Agent, or Firm—Benjamin J. Barish

[57] ABSTRACT

An endoscopic attachment to a surgical laser comprises a hollow endoscopic tube adapted to be coupled at its rear end to the surgical laser, a coupling device including a pivotable reflector in the path of the laser beam transmitted through the endoscopic tube for reflecting same to the working area at the front end of the tube, and a manipulatable joystick connected to the reflector for manipulating the laser beam to direct it through the endoscopic tube and to selected positions in the working area at the front end of the tube. The attachment is to be used with a surgical laser producing a working laser beam and a separate, visible, aiming laser beam, the latter being partially reflected by the reflector and partially transmitted through the reflector to permit viewing the working area. The reflector further includes a light-absorbing member located to absorb the visible light transmitted through the reflector from the aiming laser beam, but not to interfere with observing the working area through the eyepiece.

16 Claims, 4 Drawing Figures

ENDOSCOPIC ATTACHMENT TO A SURGICAL LASER

RELATED APPLICATION

The present application is a continuation-in-part of application Ser. No. 06/431,204 filed Sept. 30, 1982, now abandoned.

BACKGROUND OF THE INVENTION

The present invention relates to endoscopic attachments to a surgical laser.

Surgical lasers are now gaining increasing use for performing various types of surgical operations Among their many advantages are their ability to make very clean, fine cuts while minimizing damage to tissue outside the cutting line; and also their ability to readily coagulate the blood in capillaries, small veins and arteries, thereby minimizing loss of blood and keeping the wound area clean. One example of a surgical laser with respect to which the present invention is particularly useful is described in U.S. Pat. No. 3,913,582. Various types of attachments have also been devised to enhance the use of surgical lasers, some of these attachments being described in U.S. Pat. Nos. 3,865,113 and 3,865,114. Surgical lasers, however, have not yet been widely used with endoscopic attachments having long and small-diameter endoscopic tubes, because of the difficulty of directing the laser beams through such long and small-diameter tubes.

SUMMARY OF THE INVENTION

An object of the present invention is to provide an endoscopic attachment to a surgical laser to enable its use with long and small-diameter endoscopic tubes. Another object is to provide laser apparatus including such attachments.

According to a broad aspect of the present invention, there is provided an endoscopic attachment to a surgical laser, comprising a hollow endoscopic tube coupleable at its rear end to the surgical laser such as to enable the laser to transmit laser beams through the endoscopic tube and to exit therefrom onto a working area at the front end of the endoscopic tube; and a coupling device for coupling the surgical laser to the rear end of the endoscopic tube.

The coupling device includes a pivotable reflector in the path of the laser beam for reflecting it through the endoscopic tube to the working area at the front end of the tube, and a manipulatable joystick connected to the reflector for manipulating the laser beam to direct it through the endoscopic tube to selected positions in the working area at the front end of the tube.

The surgical laser produces two separate beams, namely, a working laser beam (e.g. $CO_2$) and a visible, aiming laser beam (e.g., He-Ne). An eyepiece is located coaxially with the endoscopic tube for viewing the working area. Both of the laser beams are directed along an axis perpendicular to the axis of the endoscopic tube and eyepiece, and are reflected by a pivotable reflector along the latter axis to the working area. The reflector is actually a beam-splitter, being highly reflective with respect to the working laser beam, and partially reflective and partially transmissive with respect to visible light, to permit the aiming laser beam to be viewed through the eyepiece. The attachment further includes a light-absorber member connected to the beam-splitter reflector and to the joystick so as to be moved therewith by the manipulation of the joystick. The light-absorbing member is located out of the optical path through the eyepiece to the working area, but in position to absorb the visible light from the aiming laser beam transmitted through the beam-splitter reflector. Such a device is particularly useful as a laser bronchoscope.

In a second described embodiment, the endoscopic tube includes a telescope located in front of the laser beam reflector, the endoscopic tube including a channel for the laser beam and a separate channel for viewing the working area via the telescope. Such a device is particularly useful as a laparoscope.

Further features and advantages of the invention will be apparent from the description below.

BRIEF DESCRIPTION OF THE DRAWINGS

The invention is herein described by way of example only, with reference to the accompanying drawings, wherein.

DESCRIPTION OF PREFERRED EMBODIMENTS

Figures 1, 1A:
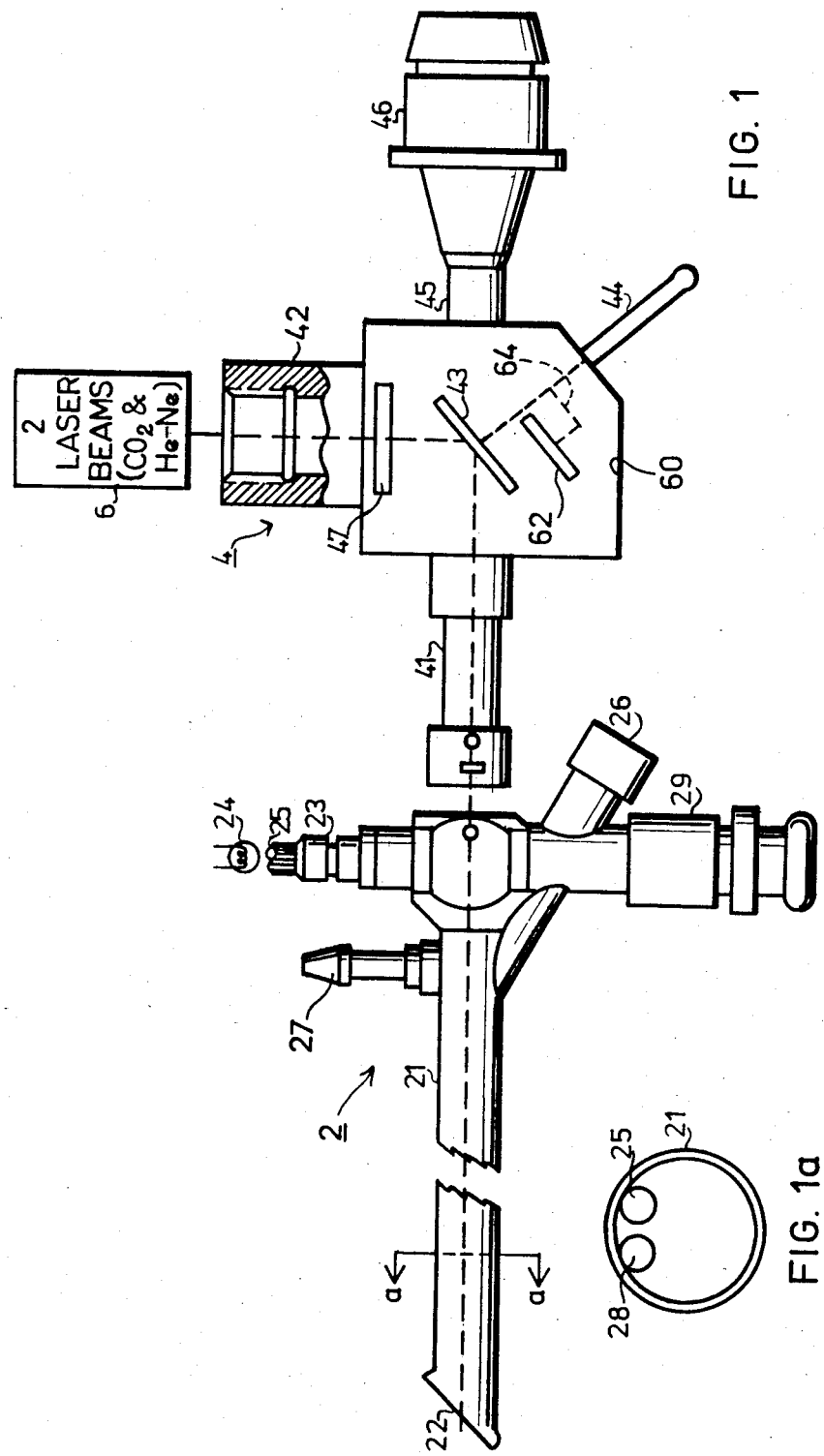
FIG. 1 illustrates one form of endoscopic attachment constructed in accordance with the invention, this form being particularly useful as a bronchoscope.
FIG. 1a is a sectional view along lines a—a of FIG. 1.

With reference to FIG. 1, the bronchoscope illustrated comprises two main parts, namely, the endoscopic tube portion, generally designated 2, and a coupling device, generally designated 4, for coupling portion 2 to a surgical laser, schematically indicated by box 6.

Part 2 of the bronchoscope illustrated in FIG. 1 comprises an endoscopic tube 21 coupleable at its rear end (right end in FIG. 1) to the coupling device 4 such as to enable the laser 6 to transmit a laser beam through the endoscopic tube 21 and to exit therefrom to a working area at the front end (left end, FIG. 1) of the endoscopic tube. The front end of the endoscopic tube 21 is preferably cut at a bias, as shown at 22.

Part 2 also includes a number of fittings for use with the endoscopic tube 21 during surgical operations. Thus, part 2 includes, at the rear end of the endoscopic tube 21, a fitting 23 for a light source 24 adapted to illuminate the rear end of a fiber-optical bundle 25 (see FIG. 1a) extending through the endoscopic tube 21 to illuminate the working area at the front end of that tube: a fitting 26 whose axis is at an angle (e.g. 45°) to that of the endoscopic tube 21, to enable a tool to be inserted through the endoscopic tube and to be manipulated by the surgeon at the working area during the surgical operation; a fitting 27 for applying suction through a tubelet 28 (FIG. 1a) extending through the endoscopic tube to the working area at the front end of the tube; and a further fitting 29 for coupling the interior of the endoscopic tube to a source of pressurized fluid, such as pressurized air, for inflating the working area at the front end of the endoscopic tube.

The coupling device 41 for coupling the laser beam to the endoscopic tube 21, includes a tube 41 adapted to be coupled to the rear end of, and to extend coaxially with, the endoscopic tube 21 of part 2; a second tube 42 for coupling to the surgical laser 6, the longitudinal axis of tube 42 being perpendicular to that of tube 41 and the endoscopic tube 21; and a reflector 43 at the intersection point of the axes of tubes 41 and 42.

Reflector 43 is connected to a joystick 44 which is manipulatable by the surgeon to direct the laser beam through the tube 44. An optical device, in the form of a telescope including an optical tube 45 and an eyepiece 46 both coaxial to the longitudinal axis of the endoscopic tube 21, is attached to the rear end of tube 21 to permit receiving the working area at the front end of the tube.

The coupling device 4 further includes a two-position mechanical shutter 47 between fitting 42 for coupling to the laser 6, and the reflector 43. The mechanical shutter 47 is operated to selectively block the laser beam from, or to transmit it to, the reflector 43 and thereby to the working area at the front end of the endoscopic tube 21.

The surgical laser 6 produces two laser beams, namely, a working beam (e.g., $CO_2$) and visible, sighting or aiming laser beam (e.g., He-Ne). Both beams are introduced via fitting 42 along an axis perpendicular to the axis of the endoscopic tube 21, and are reflected by reflector 43 along the latter axis to the working area at the front of the tube. Reflector 43 is a beam-splitter, being highly reflective with respect to the working laser beam, and partially reflective (about 50%) and partially transmissive with respect to visible light, i.e., the visible, aiming laser beam, so as to permit the aiming laser beam to be viewed through eyepiece 46.

The illustrated apparatus further includes a light-absorbing member 62 between beam-splitter reflector 43 and the inner face 60 of the coupling device 4.

Absorber member 62 is in the form of a plate of absorbing glass which is located parallel to but spaced from the beam-splitter reflector 43 on the side thereof opposite to the coupling device 42 for the surgical laser 6, i.e. between reflector 43 and the inner face 60 of the coupling device. Plate 62 is connected by a coupling schematically indicated by broken lines 64, to the joystick 44 so as to be moved with reflector 43 during its manipulation by the joystick. In addition, the absorbing glass plate 62 is located sufficiently below reflector 43 so as to absorb the visible light passing through the reflector, but out of the optical path through the eyepiece to the working area so as not to interfere with the viewing of the working area.

It was found that this arrangement substantially improves the visibility of the working area via eyepiece 46, since it eliminated the glare produced by the light from the aiming laser beam passing through reflector 43 which impinged against the inner face 60 of the fitting and was reflected back to the beam-splitter reflector 43 and then to the eyepiece 46.

As one example, plate 62 may be of Schott Filter Glass RG 850 coated with an anti-reflection coating on the face thereof facing reflector 43.

The joystick 44 may be coupled to reflector 43 in any known manner, such as by a mechanical coupling as described in U.S. Pat. No. 4,228,341 or by an electrical coupling, so as to enable the surgeon to manipulate the reflector, and thereby to manipulate the laser beams, to selected positions in the working area at the front end of the endoscopic tube 21, while that working area is being viewed via the telescope eyepiece 46.

Figures 2, 2A:
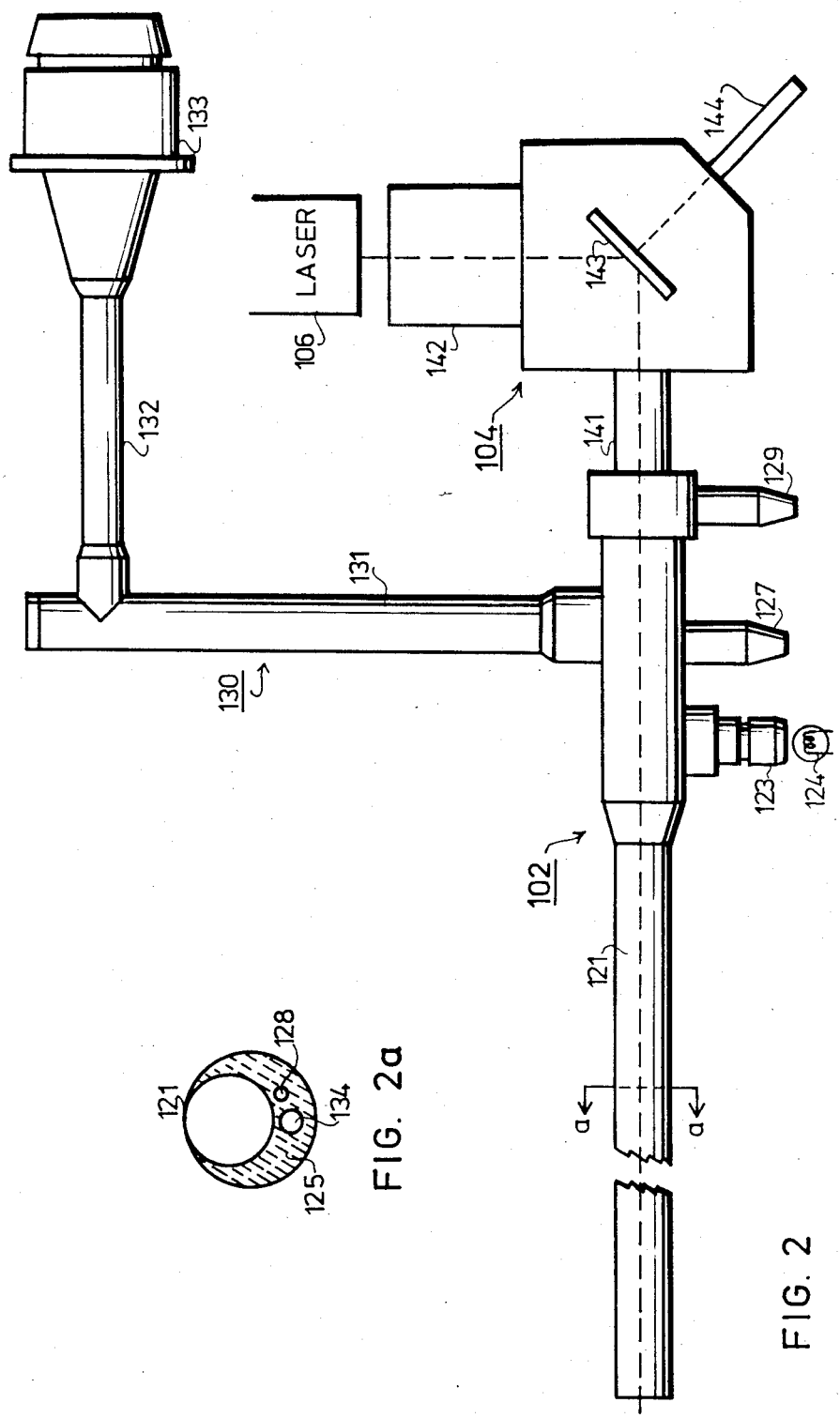
FIG. 2 illustrates a second form of endoscopic attachment constructed in accordance with the invention, this form being particularly useful as a laparoscope.
FIG. 2a is a sectional view along lines a—a of FIG. 2.

The laparoscope illustrated in FIGS. 2 also includes two main parts, namely, part 102 carrying the endoscopic tube 121, and part 104 constituting the coupling device for coupling the endoscopic tube 121 to the surgical laser, schematically indicated by box 106. The laparoscope of FIG. 2 also includes a telescope optical device to enable viewing the working area, but in this case, the telescope is carried by the endoscopic tube part 102, rather than by the coupling device part 104 as in the FIG. 1 embodiment More particularly, part 102 also includes, as part 2 in FIG. 1, in addition to the endoscopic tube 121 and at its rear end: a fitting 123 for coupling a visible light source 124 to the rear end of a fiber-optical bundle 125 (FIG. 2a) extending through the endoscopic tube 121; a suction fitting 127 for applying suction via a tubelet 128 extending through the endoscopic tube 121; and a pressurized-fluid fitting 129 for applying a pressurized fluid, such as air, via the interior of the endoscopic tube 121 to the working area at its front end. It will be noted that the laparoscope illustrated in FIG. 2 does not include a tool insertion fitting, corresponding to fitting 26 in FIG. 1, but does include the telescopic optical device.

The telescopic optical device, generally designated 130 in FIG. 2, includes a first optical tube tube 131 located at the rear of the endoscopic tube 121 with its longitudinal axis perpendicular to that of the endoscopic tube. One end of optical tube 131 is coupled to part 102, and the opposite end of optical tube 131 is coupled to a second optical tube 132 whose axis extends parallel to the longitudinal axis of the endoscopic tube 121. The outer end of optical tube 132 is provided with an eyepiece 133 to permit the surgeon to view the working area at the front end of the endoscopic tube 121 via a separate channel 134 through the endoscopic tube 121.

The coupling device 104, for coupling the endoscopic tube 121 to the surgical laser 106, includes: a first coupling tube 141 for coupling to the endoscopic tube part 102 and coaxial with the endoscopic tube 121; a second coupling tube 142 for coupling to the laser 106 perpendicular to the axis of the endoscopic tube 121; and a reflector 143 at the point of intersection of the longitudinal axis of the endoscopic tube 121 with that of coupling tube 142. The coupling device 104 further includes a joystick 144, corresponding to joystick 44 in FIG. 1, for manipulating the reflector 143, to permit the surgeon to manipulate the laser beam passing through the endoscopic tube 121 to selected positions in the working area at the front end of the endoscopic tube and also to initially direct the beam through the tube.

It will be seen that the telescopic device 130 in the laparoscope of FIG. 2 does not use the manipulatable reflector 143 provided for manipulating the laser beam, but rather uses a separate channel 134 (FIG. 2a), to view the working area at the front end of the endoscopic tube. Accordingly, the reflector 143 need only be reflective with respect to the laser beam and need not be transmissive with respect to visible light, as in the FIG. 1 embodiment. Preferably, however, the laser beam in the FIG. 2 embodiment also includes a working $CO_2$ beam and a sighting He-Ne beam as in FIG. 1.

While the invention has been described with respect to two preferred embodiments, it will be appreciated that many other variations, modifications and applications of the invention may be made.

What is claimed is:

1. An endoscopic attachment to a surgical laser, comprising:

a hollow endoscopic tube coupleable at one end, constituting its rear end, to the surgical laser such as to enable the laser to transmit a laser beam through the endoscopic tube and to exit therefrom onto a working area at the opposite end, constituting the front end of the endoscopic tube;

said hollow endoscopic tube including a fitting at its rear end for a light source to illuminate the working area at the front end of the tube;

and a coupling device for coupling the surgical laser to said rear end of the endoscopic tube; said coupling device including;

a pivotable reflector in the path of said laser beam for reflecting same through the endoscopic tube to said working area at the front end thereof; and a manipulatable joystick connected to said reflector for manipulating the laser beam to direct it through the endoscopic tube and to selected positions in said working area at the front end of the endoscopic tube;

said surgical laser producing both a working laser beam and a separate, visible, aiming laser beam; said endoscopic attachment further including an eyepiece enabling viewing the visible aiming laser beam;

said eyepiece being located coaxially with said hollow endoscopic tube at said rear thereof;

said coupling device directing both of said laser beams along an axis perpendicular to the axis of the endoscopic tube to be reflected by said pivotable reflector along said latter axis to said working area;

said pivotable reflector being highly reflective with respect to said working laser beam, and partially reflective and partially transmissive with respect to visible light to permit said aiming laser beam to be viewed through said eyepiece, said reflector further including a light absorber member connected therewith to said joystick so as to be moved with the reflector by the manipulation of said joystick;

said light absorbing member being located out of the optical path through said eyepiece to the working area, but in position to absorb the visible light of said aiming laser beam transmitted through said reflector.

2. The endoscopic attachment according to claim 1, wherein said endoscopic tube includes a further fitting having an axis at an angle to the axis of the endoscopic tube to enable a tool to be inserted therethrough and to be manipulated at the working area.

3. The endoscopic attachment according to claim 2, wherein said coupling device includes a telescope having an eyepiece disposed along the longitudinal axis of said endoscopic tube rearwardly of the reflector, said reflector being highly reflective with respect to the laser beam, and paritally reflective and partially transmissive with respect to visible light.

4. The endoscopic attachment according to claim 1, wherein said endoscopic tube includes a telescope located in front of said reflector, said endoscopic tube including a channel for the laser beam and a separate channel for viewing the working area via said telescope.

5. The endoscopic attachment according to claim 1, wherein said light absorber member is a plate of absorbing glass located parallel to but spaced from said reflector on the side thereof opposite to said coupling device for the laser beams.

6. The endoscopic attachment according to claim 5, wherein said glass plate includes an anti-reflecting coating on the face thereof facing said reflector.

7. An endoscopic attachment to a surgical laser, comprising: a hollow endoscopic tube; a coupling device for coupling, to one end of the hollow endoscopic tube constituting its rear end, a surgical laser producing both a working laser beam and a separate, visible, aiming laser beam, such as to permit both laser beams to pass through the endoscopic tube onto a working area at the opposite end of the endoscopic tube, constituting its front end; said coupling device further including a pivotable reflector in the path of said laser beams for reflecting same through the endoscopic tube to said working area at the front end thereof; a manipulatable joystick connected to said reflector for manipulating both laser beams to direct them through the endoscopic tube to selected positions in said working area at the front end thereof; an eyepiece located at the rear end of said hollow endoscopic tube and coaxially thereof; said coupling device directing both said laser beams along an axis perpendicular to the axis of the endoscopic tube to be reflected by said pivotable reflector along said latter axis to said working area; said pivotable reflector being highly reflective with respect to said working laser beam, and partially reflective and partially transmissive with respect to visible light to permit said aiming laser beam to be viewed through said eyepiece; and a light-absorbing member connected with said reflector to said joystick so as to be moved therewith by the manipulation of said joystick; said light-absorber member being located out of the optical path of said eyepiece but in position to absorb the visible light of said aiming laser beam transmitted through said reflector.

8. The endoscopic attachment according to claim 7, wherein said light absorber member is a plate of absorbing glass located parallel to but spaced from said reflector on the side thereof opposite to said coupling device for the laser beams.

9. The endoscopic attachment according to claim 8, wherein said glass plate includes an anti-reflecting coating on the face thereof facing said reflector.

10. The endoscopic attachment according to claim 7, wherein said endoscopic tube includes a further fitting having an axis at an angle to the axis of the endoscopic tube to enable a tool to be inserted therethrough and to be manipulated at the working area.

11. Laser apparatus comprising a surgical laser producing both a working laser beam and a separate, visible, aiming laser beam; a hollow endoscopic tube coupled at one end, constituting its rear end, to said surgical laser such as to permit both laser beams to pass through the endoscopic tube onto a working area at the opposite end of the endoscopic tube, constituting its front end; a pivotable beam-splitter in the path of both of said laser beams for reflecting same through the endoscopic tube to said working area at the front end thereof; a manipulatable joystick connected to said beam-splitter for manipulating the laser beams to direct them through the endoscopic tube to selected positions in said working area at the front end thereof; an eyepiece located at the rear end of said hollow endoscopic tube and coaxially therewith; said surgical laser being disposed such that both its laser beams are directed along an axis perpendicular to the axis of the endoscopic tube and are reflected by said pivotable beam-splitter along said latter axis to said working area; said pivotable beam-splitter being highly reflective with respect to said working laser beam, and partially reflective and partially transmissive with respect to visible light to permit said aiming laser beam to be viewed through said eyepiece; and a light-absorbing member connected with said beam-splitter to said joystick so as to be moved therewith by the manipulation of said joystick; said light-absorber member being located out of the optical path of said eyepiece but in position to absorb the visible light of said aiming laser beam transmitted through said beam-splitter.

12. Laser apparatus according to claim 11, wherein said light-absorber member is a plate of absorbing glass located paralled to but spaced from said beam-splitter on the side thereof opposite to said surgical laser.

13. Laser apparatus according to claim 12, wherein said glass plate includes an acute-reflecting coating on the face thereof facing said beam-splitter.

14. Laser apparatus according to claim 12, wherein said eyepiece is a part of a telescope located behind said reflector.

15. Laser apparatus according to claim 12, wherein said endoscopic tube further includes a fiber-optical bundle extending therethrough and adapted to be coupled at its rear end to a source of visible light and to transmit same to its front end to illuminate the working area in the front end of the endoscopic tube.

16. Laser apparatus according to claim 12, wherein said endoscopic tube further includes a fitting having an axis at an angle to the axis of the endoscopic tube to enable a tool to be inserted therethrough and to be manipulated at the working area.

* * * * *